(12) United States Patent
Griffin

(10) Patent No.: US 8,285,097 B2
(45) Date of Patent: Oct. 9, 2012

(54) ANNULAR SIDE FIRE OPTICAL DEVICE FOR LATERALLY REDIRECTING ELECTROMAGNETIC RADIATION

(75) Inventor: Stephen E. Griffin, Peoria, AZ (US)

(73) Assignee: AMS Research Corporation, Minnetonka, MN (US)

( * ) Notice: Subject to any disclaimer, the term of this patent is extended or adjusted under 35 U.S.C. 154(b) by 338 days.

(21) Appl. No.: 12/517,883

(22) PCT Filed: Dec. 6, 2007

(86) PCT No.: PCT/US2007/024964
§ 371 (c)(1),
(2), (4) Date: Jun. 5, 2009

(87) PCT Pub. No.: WO2008/073264
PCT Pub. Date: Jun. 19, 2008

(65) Prior Publication Data
US 2011/0002584 A1    Jan. 6, 2011

Related U.S. Application Data

(60) Provisional application No. 60/869,007, filed on Dec. 7, 2006, provisional application No. 60/869,013, filed on Dec. 7, 2006.

(51) Int. Cl.
*G02B 6/04* (2006.01)
*G02B 6/06* (2006.01)
*A61B 18/18* (2006.01)

(52) U.S. Cl. ............. 385/117; 385/31; 385/43; 606/15; 606/16

(58) Field of Classification Search ................. 385/117, 385/118
See application file for complete search history.

(56) References Cited

U.S. PATENT DOCUMENTS

| 4,381,882 A | 5/1983 | Sabine |
| 4,669,467 A | 6/1987 | Willett et al. |
| 4,672,961 A | 6/1987 | Davies |

(Continued)

FOREIGN PATENT DOCUMENTS

EP   0 689 797 A1   6/1995

(Continued)

OTHER PUBLICATIONS

U.S. Appl. No. 12/517,879, filed Jun. 5, 2009.

(Continued)

*Primary Examiner* — Michelle R Connelly
(74) *Attorney, Agent, or Firm* — Westman, Champlin & Kelly, P.A.

(57) ABSTRACT

An annular side fire optical device for laterally redirecting electromagnetic radiation comprises a tapered section of silica, a conical section of silica adjoining the tapered section and an annular beveled end surface. The tapered section of silica has a diameter that increases with distance along a longitudinal axis in a direction toward a transmitting end. The conical section of silica comprises a wall of silica surrounding a conical bore. The conical bore has a diameter that increases with distance along the longitudinal axis in a direction toward the transmitting end. The annular beveled end surface is formed in the wall of silica at the transmitting end and is angled relative the longitudinal axis such that electromagnetic radiation propagating along the longitudinal axis through the conical section is reflected by the beveled end surface at an angle that is transverse to the longitudinal axis.

20 Claims, 4 Drawing Sheets

U.S. PATENT DOCUMENTS

| | | | |
|---|---|---|---|
| 4,732,448 A | 3/1988 | Goldenberg | 385/33 |
| 4,740,047 A | 4/1988 | Abe et al. | |
| 5,061,265 A | 10/1991 | Abela et al. | |
| 5,074,632 A | 12/1991 | Potter | |
| 5,242,438 A * | 9/1993 | Saadatmanesh et al. | 606/15 |
| 5,269,777 A | 12/1993 | Doiron et al. | |
| 5,292,320 A | 3/1994 | Brown et al. | |
| 5,343,543 A | 8/1994 | Novak, Jr. et al. | |
| 5,354,294 A | 10/1994 | Chou | |
| 5,428,699 A | 6/1995 | Pon | |
| 5,486,171 A | 1/1996 | Chou | |
| 5,495,541 A | 2/1996 | Murray et al. | |
| 5,496,307 A | 3/1996 | Daikuzono | |
| 5,496,308 A | 3/1996 | Brown et al. | |
| 5,498,260 A | 3/1996 | Rink et al. | |
| 5,509,917 A | 4/1996 | Cecchetti et al. | |
| 5,512,078 A | 4/1996 | Griffin | |
| 5,530,780 A | 6/1996 | Ohsawa | |
| 5,537,499 A * | 7/1996 | Brekke | 385/31 |
| 5,562,657 A | 10/1996 | Griffin | |
| 5,571,099 A | 11/1996 | Purcell, Jr. et al. | |
| 5,638,483 A | 6/1997 | Konwitz | |
| 5,695,583 A | 12/1997 | van den Bergh et al. | |
| 5,807,390 A | 9/1998 | Fuller et al. | |
| 5,824,005 A | 10/1998 | Motamedi et al. | |
| 6,246,817 B1 | 6/2001 | Griffin | |
| 6,270,492 B1 | 8/2001 | Sinofsky | |
| 6,284,085 B1 | 9/2001 | Gwo | |
| 6,398,778 B1 | 6/2002 | Gu et al. | |
| 6,522,806 B1 | 2/2003 | James, IV et al. | |
| 6,626,582 B2 | 9/2003 | Farrar et al. | |
| 6,687,436 B2 | 2/2004 | Griffin | 385/43 |
| 6,712,526 B1 | 3/2004 | Fleenor | 385/78 |
| 6,829,411 B2 | 12/2004 | Easley | |
| 6,986,764 B2 | 1/2006 | Davenport et al. | |
| 7,909,817 B2 | 3/2011 | Griffin et al. | 606/13 |
| 8,073,297 B2 | 12/2011 | Griffin | |
| 2005/0165279 A1 | 7/2005 | Adler et al. | |
| 2006/0291061 A1 | 12/2006 | Iyama et al. | |
| 2007/0106286 A1 | 5/2007 | Harschack et al. | 606/17 |
| 2008/0287936 A1 | 11/2008 | Stinson et al. | |
| 2010/0135617 A1 | 6/2010 | Novak, Jr. et al. | |
| 2011/0038580 A1 | 2/2011 | Griffin | 385/33 |

FOREIGN PATENT DOCUMENTS

| | | |
|---|---|---|
| JP | 60250322 | 12/1985 |
| JP | 62011820 | 1/1987 |
| JP | 03111040 | 5/1991 |
| JP | 10155805 | 6/1998 |
| JP | 2001346891 | 12/2001 |
| WO | 2008073263 A1 | 6/2008 |
| WO | 2008073264 A2 | 6/2008 |

OTHER PUBLICATIONS

U.S. Appl. No. 61/118,857, filed Dec. 1, 2008.
International Search Report and Written Opinion of PCT/US2007/024963 filed Dec. 6, 2007.
International Search Report and Written Opinion of PCT/US2007/024964 filed Dec. 6, 2007.

* cited by examiner

ANNULAR SIDE FIRE OPTICAL DEVICE FOR LATERALLY REDIRECTING ELECTROMAGNETIC RADIATION

CROSS-REFERENCE TO RELATED APPLICATION

This Application is a Section 371 National Stage Application of International Application No. PCT/US2007/024964, filed Dec. 6, 2007 and published as WO 2008/073264 A3 on Jun. 19, 2008, and claims the benefit of U.S. Provisional Application Ser. No. 60/869,007 filed Dec. 7, 2006 and U.S. Provisional Application Ser. No. 60/869,013 filed Dec. 7, 2006 under 35 U.S.C. §119(e). Each of the above-referenced applications are incorporated herein by reference in their entirety.

FIELD OF THE INVENTION

Embodiments of the present invention generally relate to an optical device for laterally redirecting electromagnetic radiation for use in surgical probes, and more particularly, to an optical device configured to laterally redirect electromagnetic radiation annularly about a longitudinal axis of the device.

BACKGROUND

Electromagnetic energy, such as laser light, is used to perform various medical procedures including the destruction of diseased tissues, for example. One optical device that is used in surgical tools that perform such medical procedures is a side-firing optical device.

Side fire optical devices are typically used to redirect electromagnetic radiation (hereinafter "laser light") in an off-axis direction from the longitudinal axis of the delivery fiber and the device, typically at and angle of 74-76 degrees off axis. Conventional side-firing optical devices operate by reflecting the electromagnetic radiation off of a beveled optical surface. The redirected output laser light is transmitted through a transmitting surface, also known as a protective cap, of the device to the surgical site. The redirected output laser light typically spans a short arc, typically 26 degrees, full angle, about the longitudinal axis of the device. An exemplary side-firing optical device is disclosed in U.S. Pat. No. 5,428,699.

While such conventional side-firing optical devices are useful for the treatment of specifically targeted material (i.e., spot treatments), they are not designed to provide substantially uniform treatment of tissue surrounding the device in a radial direction.

SUMMARY

Embodiments of the invention are directed to an annular side fire optical device for laterally redirecting electromagnetic radiation. In one embodiment the device includes a tapered section of silica, a conical section of silica adjoining the tapered section and an annular beveled end surface. The tapered section of silica has a diameter that increases with distance along a longitudinal axis in a direction toward a transmitting end. The conical section of silica comprises a wall of silica surrounding a conical bore. The conical bore has a diameter that increases with distance along the longitudinal axis in a direction toward the transmitting end. The annular beveled end surface is formed in the wall of silica at the transmitting end and is angled relative the longitudinal axis such that electromagnetic radiation propagating along the longitudinal axis through the conical section is reflected by the beveled end surface at an angle that is transverse to the longitudinal axis.

Another embodiment of the invention is directed to a method of forming an annular side fire optical device for laterally redirecting electromagnetic radiation. In the method, a section of silica tubing having a bore, a longitudinal axis, a receiving end and a transmitting end is provided. An annular beveled end surface is formed in the transmitting end of the silica tubing. A portion of the tubing adjacent the receiving end is heated and transformed into a tapered section and a conical section that adjoins the tapered section. The tapered section comprises a length of solid silica having a diameter that increases with distance traveled along the longitudinal axis in the direction from the receiving end to the transmitting end. The conical section comprises a wall of silica surrounding a conical bore having a diameter that increases with distance traveled along the longitudinal axis in the direction from the tapered section to the transmitting end.

This Summary is provided to introduce a selection of concepts in a simplified form that are further described below in the Detailed Description. This Summary is not indented to identify key features or essential features of the claimed subject matter, nor is it intended to be used as an aid in determining the scope of the claimed subject matter. The claimed subject matter is not limited to implementations that solve any or all disadvantages noted in the Background.

DETAILED DESCRIPTION OF ILLUSTRATIVE EMBODIMENTS

Figure 1:
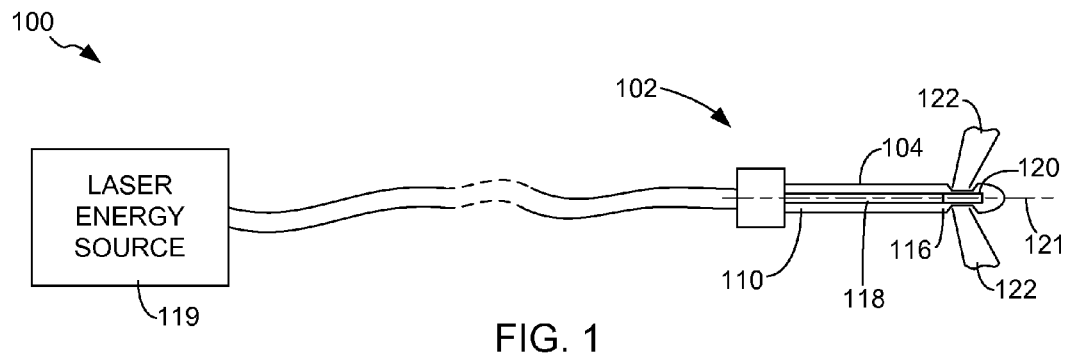
FIG. 1 is a simplified diagram of an exemplary laser surgical system and surgical tool in accordance with embodiments of the invention.

FIG. 1 is a simplified diagram of an exemplary laser surgical system 100 in accordance with embodiments of the invention. The system 100 includes a surgical tool 102, in which embodiments of the present invention are useful. The surgical tool 102 includes an outer sheath 104. The surgical tool 102 can be used to perform medical procedures in which tissues of a surgical site of a patient are exposed to electromagnetic radiation, preferably in the form of laser light, such as in the treatment of an enlarged prostate gland. The outer sheath 104 can be formed of series 300 stainless steel or other suitable material, such as aluminum, thermal plastics, or other materials. The outer sheath 104 has a circular cross-section with a diameter sufficient to support the components of the surgical tool 104.

A cannula 110, having a circular cross-section, is positioned within the sheath 104. A probe 116 is provided in the cannula 110. The probe 116 includes a delivery fiber optic 118 for communicating or transmitting electromagnetic radiation from a source, such as laser energy source 119, to an annular side fire optical device 120, which is formed in accordance with embodiments of the invention described below. The annular side fire optical device 120 redirects the electromagnetic radiation (hereinafter "laser light") transmitted by the fiber optic 118 laterally or transverse to a longitudinal axis 121 of the device 120 onto the surgical site, as illustrated by laser light 122 in FIG. 1. Embodiments of the annular side fire optical device 120 can transmit an annular ring (i.e., full 360 degrees around the device 120) of redirected laser light 122 radially from the longitudinal axis 121, as illustrated in the simplified front view of the device 120 provided in FIG. 2A.

Accordingly, unlike side fire optical devices of the prior art that redirect laser energy that is propagating along the axis of a fiber in primarily one direction off that axis, with the included angle of the typically inhomogeneous energy spread about the fiber axis defined by the numerical aperture (NA) of the fiber itself, the annular side fire optical device 120 of the present invention redirects laser energy substantially uniformly about the entire circumference of the fiber independent of the base fiber NA.

The surgical tool 102 may also include a saline inflatable balloon configured to secure the position of the probe 116 at the surgical site and for other purposes known in the art. Additionally, the surgical tool 102 may include a scope for viewing the surgical site.

Figure 3:
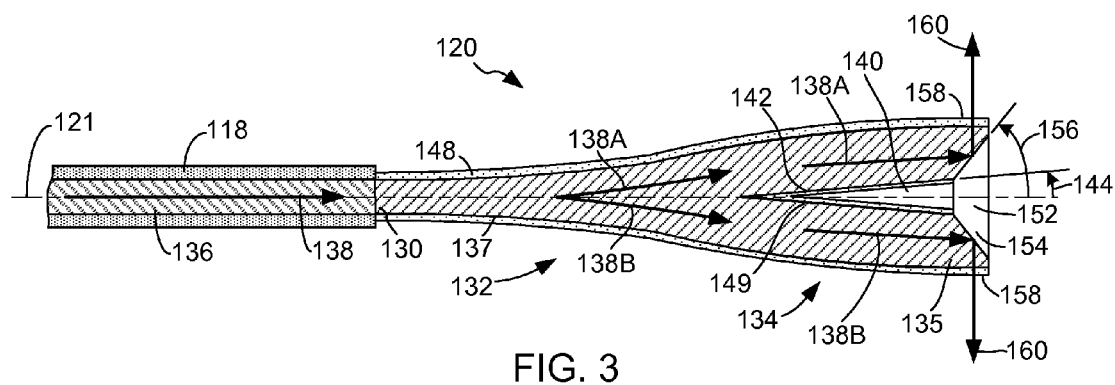
FIGS. 3-5 are cross-sectional views of an annular side fire optical device for laterally redirected electromagnetic radiation in accordance with embodiments of the invention.

FIG. 3 is a side cross-sectional view of the annular side fire optical device 120 in accordance with embodiments of the invention. The components of the annular side fire optical device 120 preferably have a cylindrical shape. That is, cross-sections of the components of the annular side fire optical device 120 taken in a plane that is perpendicular to the longitudinal axis 124 of the device 120 are generally circular.

One embodiment of the annular side fire optical device 120 comprises a receiving end 130, a tapered section 132, a conical section 134 and a transmitting end 135. In one embodiment, the receiving end 130 and the sections 132 and 134 are each formed of silica. The receiving end 130 is fused or otherwise integrally coupled physically and optically to the core fiber 136 of the delivery fiber optic 118 such that the device 120 can receive laser light delivered by the fiber optic 118 from a suitable source, such as the laser energy source 119 shown in FIG. 1.

An exterior wall or surface 137 of the tapered section 132 and the conical section 134 is shaped in accordance with conventional principles to maintain total internal reflection of the laser light 138 received from the delivery core fiber 136. The tapered section 132 of the device 120 gradually increases the diameter of the silica from the receiving section 130 to the conical section 134 to preserve the desired shape of the exterior surface 137. That is, the diameter of the tapered section increases with distance traveled along the longitudinal axis 121 from the receiving end 130 toward to the transmitting end 135, as shown in FIG. 3.

One embodiment of the conical section 134 of the device 120 comprises a wall of silica 139 and a conical bore 140. The diameter of the conical bore increases with distance traveled along the longitudinal axis 121 from the receiving end 130 toward to the transmitting end 135, as shown in FIG. 3. The conical bore 140 is defined by an interior wall or surface 142 of the silica having an angle 144 relative to the longitudinal axis 121. The angle 144 can be selected, in accordance with conventional principles, such that substantially all of the laser light 138 is internally reflected off the interior wall 142 to maintain the propagation of the laser light 138 along the longitudinal axis 121 within the conical section 134. For example, the laser light 138 should at least be subject to total internal reflection off the interior wall 142 when the angle of the interior wall or surface 142 relative to the longitudinal axis 121 is equal to, or less than, the angle of the external wall or surface 137 of the conical section 134 relative to the longitudinal axis, regardless of whether the surface 142 includes the cladding 149 or not.

As a result, the laser light 138 received from the delivery fiber optic 118 propagate along the longitudinal axis 121 and through the receiving end 130, the tapered section 132 and the conical section 134 due to the shape of the exterior surface 137 and the interior surface 142 of the device 120. The laser light is further directed around the conical bore 140 by the wall 142 and toward a transmitting end 135, as illustrated by arrows 138A and 138B.

In one embodiment, the exterior surfaces of the receiving end 130, the tapered section 132 and the conical section 134 are covered in a cladding 148, such as fluorine-doped silica. In another embodiment, a cladding 149 covers at least a portion of the interior wall 142 of the conical section 134.

A chamfer 152 is formed at the transmitting end 135 of the device 120. The chamfer 152 is formed using conventional techniques such as laser polishing and machine polishing. The chamfer 152 forms an annular beveled end surface 154 that is polished to form an optical surface that is angled relative to the longitudinal axis 121 at an angle 156. In one embodiment, the annular beveled end surface 154 is coaxial to the longitudinal axis 121. The angle 156 is selected, in accordance with conventional principles, to provide substantially total internal reflection of the laser light 138A and 138B propagating along the longitudinal axis 121 within the conical section 134, such that the laser light 138A and 138B are redirected laterally through an annular transmitting surface 158, as illustrated by redirected output laser light 160. The angle 156 is typically in the range of 37-45 degrees. In one embodiment, the laser light 160 is transmitted at approximately 90 degrees to the longitudinal axis 121.

Figure 2A:
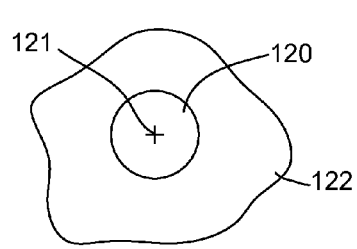
FIGS. 2A-D are simplified front views of an annular side fire optical device illustrating electromagnetic radiation output patterns, in accordance with embodiments of the invention.
Figure 2B:
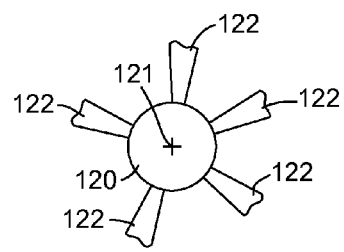
Figure 2C:
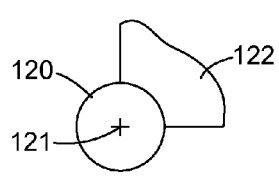
Figure 2D:
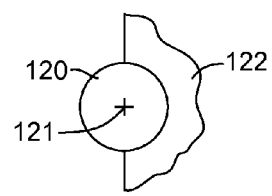

As a result, the redirected output laser light 160 is transmitted in an annular ring around the longitudinal axis 121 of the device 120 as illustrated in FIG. 2A. Thus, embodiments of the device 120 are configured to redirect the laser light 138 laterally such that the redirected output laser light 160 is transmitted in first and second opposite directions, as shown in FIGS. 2A and 3.

In other embodiments, portions of the annular transmitting surface 158 are configured to block or diffuse the redirected output laser light 160 reflected from the beveled end surface 154 such that the redirected output laser light 160 is transmitted radially from the transmitting end 135 in a desired pattern. The pattern can comprise one or more continuous arcs of laser light 160 of varying degrees, such as that illustrated in FIGS. 2A-D. Other patterns of virtually any desired angle can also be established through the blocking of the redirected output laser light 160 from the transmitting surface 158. Exemplary techniques for blocking or altering the redirected laser light 160 at the transmitting surface 158 include the use of non-planar chamfer surfaces 154 and partial metal coatings on the planar chamfer surface 154.

Figure 4:
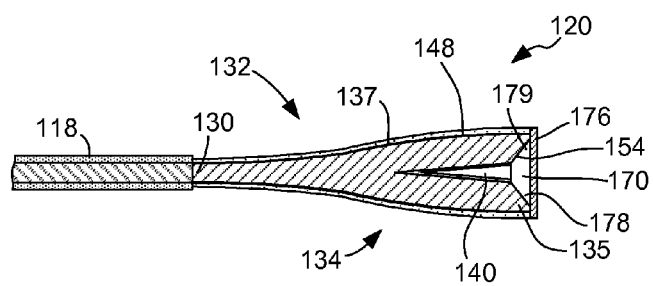
Figure 5:
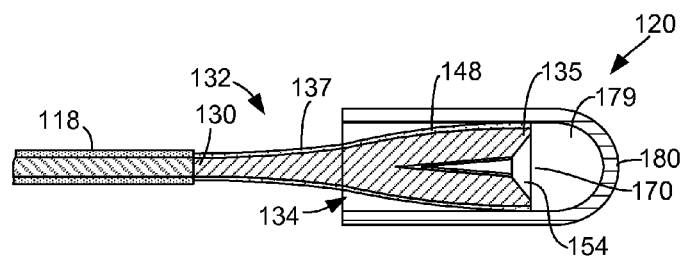

For surgical applications, such as coagulation of tissue in a gastro-intestinal medical application, it is necessary to create a sufficient interface with the beveled end surface 154 to ensure that it does not become transmissive when in contact with fluid. In one embodiment, a cover is formed over the beveled end surface 154 to create an air interface 170 at the beveled end surface 154, as shown in the side cross-sectional view of FIG. 4. In one embodiment, the cover comprises a silica plate or window 176 (FIG. 4) that is fused or otherwise connected to the peripheral edge of the chamfered opening 178, such as to the cladding 148, in accordance with conventional techniques. The plate 176 seals an interior cavity 179 to maintain the desired air interface 170 at the beveled end surface 154. In another embodiment, the cover is formed by a cap member 180, such as that conventionally used in side fire optical devices. The cap member 180 is placed over the conical section 134 to seal the interior cavity 179 and form the desired air interface 170 at the beveled end surface 154, as illustrated in the simplified side cross-sectional view of FIG. 5. In one embodiment, the cap member 180 is fused to the cladding 148 (as shown) or the exterior surface 137.

Figure 6:
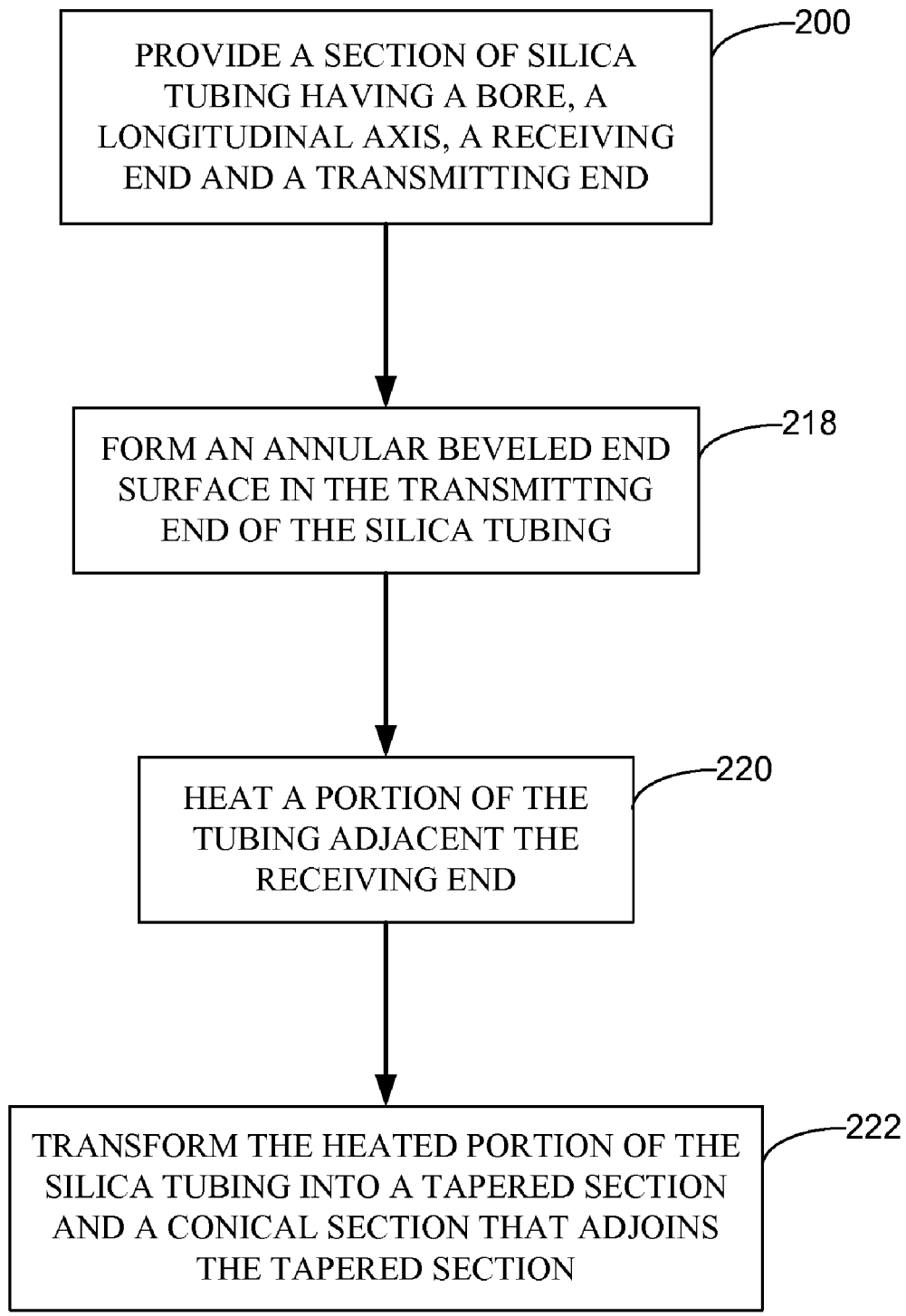
FIG. 6 is a flowchart illustrating a method of forming an annular side fire optical device for laterally redirecting electromagnetic radiation, in accordance with embodiments of the invention.

FIG. 6 is a flowchart illustrating an exemplary method of manufacturing an annular side fire optical device 120 in accordance with the embodiments described above. Elements designated by the same numbers as those used in FIGS. 2-5 generally designate the same or similar (i.e., related) elements.

Figure 7:
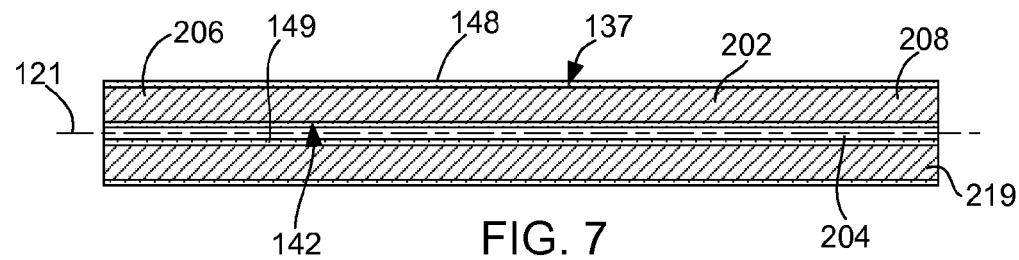
FIG. 7 is a cross-sectional view of a section of silica tubing in accordance with embodiments of the invention.

At step 200, a section of silica tubing 202, shown in FIG. 7, having a bore 204, a longitudinal axis 121, a receiving end 206 and a transmitting end 208 (135) is provided. In one embodiment, the section of silica tubing 202 includes cladding 148 on the exterior surface 212 and/or cladding 149 on the surface 216 of the bore 204. In one embodiment, when the silica tubing 202 includes the cladding 149 on the surface 142 of the bore 204, the cladding 149 is removed from within the bore 204 from the receiving end 206 up to a position that is adjacent the transmitting end 208, as shown in FIG. 8.

Figure 8:
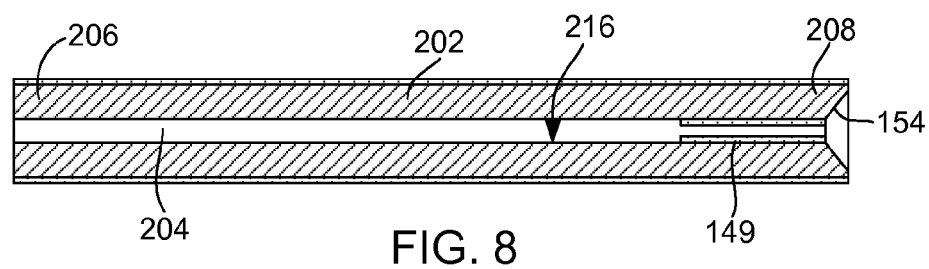
FIG. 8 is a cross-sectional view of a section of silica tubing illustrating steps of the method of forming an annular side fire optical device in accordance with embodiments of the invention.

At step 218, an annular beveled end surface 154 is formed in the transmitting end 208 of the silica tubing 202, as shown in FIG. 8. In one embodiment, the beveled end surface 154 is formed by forming a chamfer at the transmitting end 208 of the tubing 202. The chamfer can be formed using any conventional technique, such as laser or machine cutting and polishing the end surface 219 (FIG. 7) of the transmitting end 208 of the cylindrical silica wall of the tubing 202. In one embodiment, the annular beveled end surface 154 is formed such that the beveled end surface 154 is oriented at an angle 156 relative to a longitudinal axis 121, as shown in FIG. 3.

At step 220, the silica tubing 202 is heated. In one embodiment, the tubing 202, such as the central portion 221, is heated to a temperature of approximately 1800 degrees Celsius such that the tubing 202 becomes malleable and portions melt. In one embodiment, the heating step 220 involves rotating the tubing 202 in a laser beam in order to uniformly heat the circumference of the tubing 202. Other techniques for heating the tubing 202 to the desired temperature can also be employed.

Figure 9:
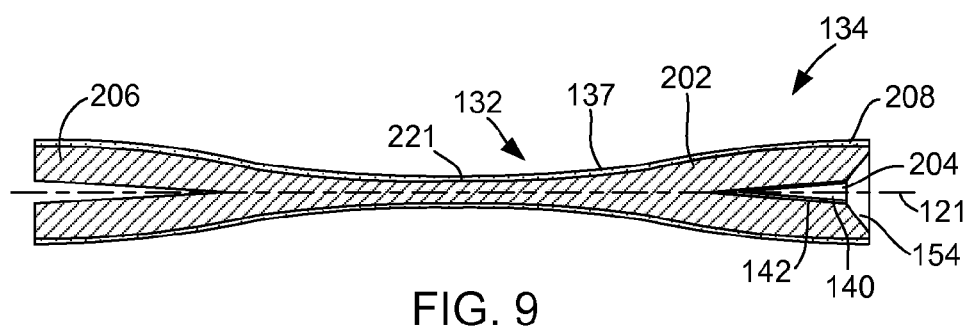
FIG. 9 is cross-sectional view of a section of silica tubing after several steps of the method have been performed.

At step 222, the heated portion of the silica tubing 202 is transformed into a tapered section 132 and a conical section 134 that adjoins the tapered section 132, as shown in FIG. 9. One embodiment of the transforming step 222 comprises collapsing the heated portion of the silica tubing 202 in a radial direction relative to the longitudinal axis 121 and stretching the heated portion of the silica tubing 202 in an axial direction corresponding to the longitudinal axis 121. This collapsing and stretching of the tubing 202 reduces the diameter of the bore 204 to zero in the central portion 221 to form the tapered section 132 that comprises a length of solid silica having a diameter that increases with distance traveled in the direction from the receiving end 206 to the transmitting end 208, as shown in FIG. 9 and discussed above with reference to FIG. 3. The formation of the tapered section 132 also collapses a portion of the bore 204 that is adjacent the transmitting end 208. The collapsed bore 204 produces a conical bore 140 that is surrounded by the wall of the silica tubing 202. The conical bore 140 has a diameter that increases with distance traveled along the longitudinal axis 121 in the direction from the tapered section 132 to the transmitting end 208, as shown in FIG. 9 and discussed above with reference to FIG. 3.

In one embodiment of the transforming step 222, the exterior surface 137 of the tapered section 132 and the conical section 134 is shaped to promote substantially total internal reflection of electromagnetic radiation propagating substantially along the longitudinal axis 121 and through the tapered section. This can be accomplished in accordance with conventional techniques such as those discussed in U.S. Pat. Nos. 5,512,078 and 6,687,436.

In one embodiment, the tapered section 132 is cut in the central portion 221 to form the receiving end 130, shown in FIG. 3. The receiving end 130 is then fused to delivery fiber 136 (FIG. 3) to optically and physically couple the device 120 to the fiber 136. In one embodiment, the central portion 221 is initially collapsed down to a diameter that is less than that of the delivery fiber 136 in step 222 and the central portion 221 is cut at a location where the diameter matches that of the delivery fiber 136. The receiving end 130 is then fused to the delivery fiber 136.

In another embodiment, when the exterior surface 137 has cladding 148, the central portion 221 is initially collapsed down to a diameter that is less than that of the delivery fiber 136 in step 222 and the delivery fiber 136 is up-tapered to roughly twice its original diameter over a few millimeters. The central portion 221 is then cut to form the receiving end 130 having a diameter that matches the up-tapered diameter of the delivery fiber 136. The receiving end 130 is then fused to the delivery fiber 136.

In one embodiment of step 222, an interior surface 142 of the conical bore 140 is shaped to promote substantially total internal reflection of electromagnetic radiation received from the tapered section 132 and propagating along the longitudinal axis 121.

In one embodiment of step 218, the beveled end surface 154 is formed at an angle relative to the longitudinal axis such that electromagnetic radiation (laser light 138) propagating along the longitudinal axis 121 through the conical section 134 is reflected by the beveled end surface 154 at an angle 156 that is transverse to the longitudinal axis 121, as indicated by laser light 160 shown in FIG. 3.

In accordance with one embodiment of the method, an annular transmitting surface 158 is formed on the exterior surface 137 of the transmitting end 208 (135) and electromagnetic radiation 160 that is reflected by the beveled end surface 154 is transmitted through the annular transmitting surface 158.

In one embodiment, an air interface 170 is formed at the annular beveled end surface 154. In one embodiment, a cover, such as plate 176 (FIG. 4) or a cap member 180 (FIG. 5) is attached to the exterior surface 137 or the cladding 148 to form the desired air interface 170, as discussed above.

Laser light 138 delivered through the fiber 136 is received at the receiving end 130 and it internally reflects within the tapered section 132 thereby propagating along the longitudinal axis 121 toward the conical section 134, as shown in FIG. 3. When the laser light reaches the conical section 134, the laser light 138 internally reflects within the conical section 134 including reflecting off of the interior side of the exterior wall or surface 137 as well as the surface 142 of the conical bore 140, as represented by arrows 138A and 138B. Finally, the laser light 138 strikes the annular beveled surface 154, which redirects the light laterally through the transmitting surface 158, as indicated by arrows 160. In one embodiment, the redirected output laser light 160 extends radially from the device 120 over a 360 degree arc or ring.

The laser light 160 transmitted by the device can be used for many different purposes. Some exemplary purposes include cutting holes in materials including the use of lower amounts of energy to cut larger holes in materials than standard beams. Additionally, the annular ring of laser light enables a cylindrical solid to be removed from a material while a standard spot beam must vaporize all of the material.

Although the present invention has been described with reference to preferred embodiments, workers skilled in the art will recognize that changes may be made in form and detail without departing from the spirit and scope of the invention.

What is claimed is:

1. An annular side fire optical device for laterally redirecting electromagnetic radiation, the device comprising:
    a tapered section of silica having a diameter that increases with distance along a longitudinal axis in a direction toward a transmitting end;
    a conical section of silica adjoining the tapered section of silica and comprising a wall of silica having an interior surface surrounding a conical bore, the conical bore having a diameter that increases with distance along the longitudinal axis in a direction toward the transmitting end; and
    an annular beveled end surface formed in the wall of silica at the transmitting end, wherein the beveled end surface is angled relative to the longitudinal axis such that electromagnetic radiation propagating along the longitudinal axis through the conical section is reflected by the beveled end surface at an angle that is transverse to the longitudinal axis;
    wherein:
        the interior surface of the conical bore is at a first angle to the longitudinal axis;
        the beveled end surface is angled at a second angle to the longitudinal axis; and
        the first and second angles are different.

2. The device of claim 1, further comprising a delivery fiber core optically coupled to a receiving end of the tapered section that is opposite the transmitting end.

3. The device of claim 1, further comprising a cover over the transmitting end, the cover and the beveled surface defining an interior cavity.

4. The device of claim 3, wherein the cover comprises silica fused to a peripheral edge of the beveled end surface.

5. The device of claim 1, wherein electromagnetic radiation received from the tapered section and propagating along the longitudinal axis is reflected within the conical section.

6. The device of claim 1, wherein the tapered section comprises an exterior surface that is angled relative to the longitudinal axis such that electromagnetic radiation received at a receiving end and propagating along the longitudinal axis is reflected within the tapered section.

7. The device of claim 1, wherein the conical section comprises an exterior surface that is angled relative to the longitudinal axis such that electromagnetic radiation received at a receiving end and propagating along the longitudinal axis is reflected within the conical section.

8. The device of claim 1, further comprising an annular transmitting surface at the transmitting end adjacent the annular beveled surface, wherein electromagnetic radiation traveling from a receiving end toward the transmitting end that is reflected by the beveled portion is transmitted through the annular transmitting surface.

9. The device of claim 8, wherein the conical bore is displaced along the longitudinal axis toward the receiving end from the annular beveled end surface and the annular transmitting surface.

10. The device of claim 1, wherein the annular beveled end surface is coaxial to the longitudinal axis.

11. The device of claim 1, further comprising cladding on the interior surface.

12. A method of forming an annular side fire optical device for laterally redirecting electromagnetic radiation, the method comprising:
    providing a section of silica tubing having a bore, a longitudinal axis, a receiving end and a transmitting end;
    forming an annular beveled end surface having a first angle to the longitudinal axis in the transmitting end of the silica tubing;
    heating a portion of the tubing adjacent the receiving end;
    transforming the heated portion of the silica tubing into a tapered section and a conical section that adjoins the tapered section, wherein:
        the tapered section comprises a length of solid silica having a diameter that increases with distance traveled along the longitudinal axis in the direction from the receiving end to the transmitting end;
        the conical section comprises a wall of silica surrounding a conical bore having a diameter that increases with distance traveled along the longitudinal axis in the direction from the tapered section to the transmitting end; and
        an interior surface of the conical bore is at a second angle to the longitudinal axis that is different from the first angle.

13. The method of claim 12, wherein forming an annular beveled end surface comprises forming the beveled end surface at an angle relative to the longitudinal axis such that electromagnetic radiation propagating along the longitudinal axis through the conical section is reflected by the beveled end surface at an angle that is transverse to the longitudinal axis.

14. The method of claim 13, further comprising forming an annular transmitting surface on an exterior surface of the transmitting end, wherein electromagnetic radiation that is reflected by the beveled end surface is transmitted through the annular transmitting surface.

15. The method of claim 12, further comprising forming an air interface at the annular beveled end surface including forming a cover over the annular beveled end surface.

16. The method of claim 12, wherein transforming the heated portion of the silica tubing into a tapered section and a conical section that adjoins the tapered section comprises forming an exterior surface of the tapered section and the conical section that is shaped to promote substantially total internal reflection of electromagnetic radiation received at the receiving end and propagating along the longitudinal axis.

17. The method of claim 12, wherein transforming the heated portion of the silica tubing into a tapered section adjacent the receiving end and a conical section at the transmitting end that adjoins the tapered section comprises forming the interior surface of the conical bore to promote substantially total internal reflection of electromagnetic radiation received from the tapered section and propagating along the longitudinal axis.

18. The method of claim 12, further comprising optically coupling the receiving end to a delivery core fiber.

19. A method of forming an annular side fire optical device for laterally redirecting electromagnetic radiation, the method comprising:

provide a section of silica tubing having a bore, a longitudinal axis, a receiving end and a transmitting end;

forming an annular beveled end surface in the transmitting end of the silica tubing;

heating a portion of the tubing adjacent the receiving end;

transforming the heated portion of the silica tubing into a tapered section and a conical section that adjoins the tapered section comprising collapsing the heated portion of the silica tubing in a radial direction relative to the longitudinal axis and stretching the heated portion of the silica tubing in an axial direction corresponding to the longitudinal axis, wherein:

the tapered section comprises a length of solid silica having a diameter that increases with distance traveled along the longitudinal axis in the direction from the receiving end to the transmitting end; and the conical section comprises a wall of silica surrounding a conical bore having a diameter that increases with distance traveled along the longitudinal axis in the direction from the tapered section to the transmitting end.

20. The method of claim 19, wherein transforming the heated portion of the silica tubing into a tapered section and a conical section that adjoins the tapered section comprises removing cladding from the silica tubing that is within the bore of the tubing.

* * * * *